US00PP17433P2

(12) United States Plant Patent
Bergman

(10) Patent No.: US PP17,433 P2
(45) Date of Patent: Feb. 20, 2007

(54) ***CHRYSANTHEMUM* PLANT NAMED 'YOYUKON'**

(50) Latin Name: *Chrysanthemum×morifolium*
Varietal Denomination: Yoyukon

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 29 days.

(21) Appl. No.: 11/157,454

(22) Filed: Jun. 21, 2005

(51) Int. Cl.
*A01H 5/00* (2006.01)

(52) U.S. Cl. ..... Plt./288
(58) Field of Classification Search ..... Plt./288
See application file for complete search history.

(56) References Cited

U.S. PATENT DOCUMENTS

PP11,997 P2 * 7/2001 VandenBerg ..... Plt./288
2006/0143752 P1 * 6/2006 Boeder ..... Plt./288

OTHER PUBLICATIONS

UPOV ROM GTITM Computer Database, GTI Jouve Retrieval Software 2006/05 Citation for Yoyukon.*

* cited by examiner

*Primary Examiner*—Wendy Haas
(74) *Attorney, Agent, or Firm*—C. A. Whealy

(57) ABSTRACT

A new and distinct cultivar of *Chrysanthemum* plant named 'Yoyukon', characterized by its uniform and upright plant habit; strong growth habit; dark green-colored foliage; uniform flowering response and habit; best grown unpinched and as a disbud-type; early flowering habit; decorative incurve-type inflorescences; white-colored ray florets; and good postproduction longevity with plants maintaining good substance and color for about three weeks in an interior environment.

2 Drawing Sheets

Botanical designation: *Chrysanthemum×morifolium.*
Cultivar denomination: 'Yoyukon'.

BACKGROUND OF THE INVENTION

The present Invention relates to a new and distinct cultivar of *Chrysanthemum* plant, botanically known as *Chrysanthemum×morifolium* and hereinafter referred to by the name 'Yoyukon'.

The new *Chrysanthemum* is a product of a planned breeding program conducted by the Inventor in Salinas, Calif. and Alva, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* originated from a cross-pollination made in November, 1999 in Salinas, Calif., of a proprietary selection of *Chrysanthemum×morifolium* identified as code number YB-4699, not patented, as the female, or seed, parent with a proprietary selection of *Chrysanthemum×morifolium* identified as code number YB-4976, not patented, as the male, or pollen, parent. The new *Chrysanthemum* was discovered and selected by the Inventor as a single flowering plant within the progeny of the stated cross-pollination grown in a controlled environment in Alva. Fla. in November, 2000. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Alva, Fla. in March, 2001. Asexual reproduction by cuttings has shown that the unique features of this new *Chrysanthemum* are stable and reproduced true to type in successive generations.

SUMMARY OF THE INVENTION

The cultivar Yoyukon has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yoyukon'. These characteristics in combination distinguish 'Yoyukon' as a new and distinct *Chrysanthemum:*

1. Uniform and upright spreading plant habit.
2. Strong growth habit.
3. Dark green-colored foliage.
4. Uniform flowering response and habit.
5. Best grown unpinched and as a disbud-type.
6. Early flowering, eight week response time.
7. Large decorative incurve-type inflorescences.
8. White-colored ray florets.
9. Good postproduction longevity with plants maintaining good substance and color for about three weeks in an interior environment.

Plants of the new *Chrysanthemum* can be compared to plants of the female parent selection. Plants of the new *Chrysanthemum* differ from plants of the female parent selection primarily in ray floret coloration as plants of the female parent selection have pink-colored ray florets.

Plants of the new *Chrysanthemum* can be compared to plants of the male parent selection. Plants of the new *Chrysanthemum* differ from plants of the male parent selection primarily in floret formation as plants of the male parent selection have disc florets.

Plants of the new *Chrysanthemum* can be compared to plants of the cultivar Yokodiak, disclosed in U.S. Plant Pat. No. 11,997. In side-by-side comparisons conducted in Alva, Fla., plants of the new *Chrysanthemum* differed from plants of the cultivar Yokodiak in the following characteristics:

1. Plants of the new *Chrysanthemum* had larger inflorescences than plants of the cultivar Yokodiak.
2. Plants of the new *Chrysanthemum* and the cultivar Yokodiak differed in inflorescence form as plants of the cultivar Yokodiak had decorative quilled-type inflorescences.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph of the first sheet comprises a side perspective view of typical flowering plants of 'Yoyukon' grown as disbud-types.

The photograph on the second sheet comprises a close-up view of a typical inflorescence of 'Yoyukon' grown as disbud-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercial potted *Chrysanthemum* production. During the production of these plants, the following conditions were measured: day temperatures, 21° C. to 27° C.; night temperatures, 17° C. to 19° C.; and light levels, 5,000 to 6,000 foot-candles. Four unrooted cuttings were directly stuck in 15-cm containers and exposed to long day/short night conditions. About two weeks later, the photoinductive short day/long night treatments were initiated. Plants used for the description were grown as disbud-types. Measurements and numerical values represent averages of typical flowering plants.

Botanical classification: *Chrysanthemum×morifolium* cultivar Yoyukon.

Commercial classification: Decorative incurve-type potted *Chrysanthemum.*

Parentage:

*Female, or seed, parent.*—Proprietary selection of *Chrysanthemum×morifolium* identified as code number YB-4699, not patented.

*Male, or pollen, parent.*—Proprietary selection of *Chrysanthemum×morifolium* identified as code number YB-4976, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Herbaceous decorative incurve-type potted *Chrysanthemum* that is best grown unpinched and as a disbud-type. Upright and uniformly mounded crown; strong growth habit.

*Plant height.*—About 27.5 cm.

*Plant width.*—About 32 cm.

*Peduncles.*—Length: About 22.5 cm. Diameter: About 3.5 mm. Internode length: About 1.2 cm. Strength: Strong. Texture: Pubescent. Color: Close to 146A.

*Foliage description.*—Arrangement: Alternate; simple. Length: About 8.3 cm. Width: About 6 cm. Apex: Mucronate. Base: Truncate. Margin: Palmately lobed, sinuses between lateral lobes parallel to convergent. Texture, upper and lower surfaces: Pubescent. Color: Developing and fully expanded foliage, upper surface: Darker green than 147A. Developing and fully expanded foliage, lower surface: Close to 147B. Venation, upper surface: Close to 147A. Venation, lower surface: 146A to 147B. Petiole length: About 2.75 cm. Petiole diameter: About 3 mm. Petiole texture, upper and lower surfaces: Pubescent. Petiole color, upper and lower surfaces: Close to 146A.

Inflorescence description:

*Appearance.*—Decorative incurve-type inflorescence form. Inflorescences borne on terminals above foliage. Disk and ray florets develop acropetally on a capitulum. Inflorescences not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to two weeks of long day/short night conditions followed by photoinductive short day/long night conditions flower about eight weeks later.

*Postproduction longevity.*—Inflorescences maintain good color and substance for about three weeks in an interior environment.

*Quantity of inflorescences.*—Grown as a disbud-type, only one inflorescence is allowed to develop per lateral branch.

*Inflorescence bud.*—Height: About 7.5 mm. Diameter: About 8 mm. Shape: Oblate. Color: Close to 146A.

*Inflorescence diameter.*—Large, about 12.5 cm.

*Inflorescence height.*—About 4.9 cm.

*Diameter of disc.*—No disc florets observed.

*Receptacle diameter.*—About 1.3 cm.

*Receptacle height.*—About 9 mm.

*Ray florets.*—Length: About 6.5 cm. Length, corolla tube: About 4.5 cm. Width, apex: About 8 mm. Width, corolla tube: About 4 mm. Shape: Quilled. Apex: Acute or emarginate. Base: Fused into a corolla tube. Margin: Entire. Orientation: Incurved. Texture, upper and lower surfaces: Smooth, glabrous; satiny. Number of ray florets per inflorescence: About 355 arranged in numerous whorls. Color: When opening and fully opened, upper surface: Close to 155D. When opening and fully opened, lower surface: Close to 155D.

*Phyllaries.*—Quantity per inflorescence: About 30 arranged in about three whorls. Length: About 9 mm. Width: About 4 mm. Shape: Lanceolate. Apex: Acute. Base: Truncate. Margin: Entire. Texture, upper surface: Waxy, smooth. Texture, lower surface: Pubescent. Color, upper and lower surfaces: Close to 146A.

*Reproductive organs.*—Androecium: Not observed on ray florets. Gynoecium: Present on ray florets. Style length: About 6.5 mm. Style color: Close to 144C. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yoyukon', as illustrated and described.

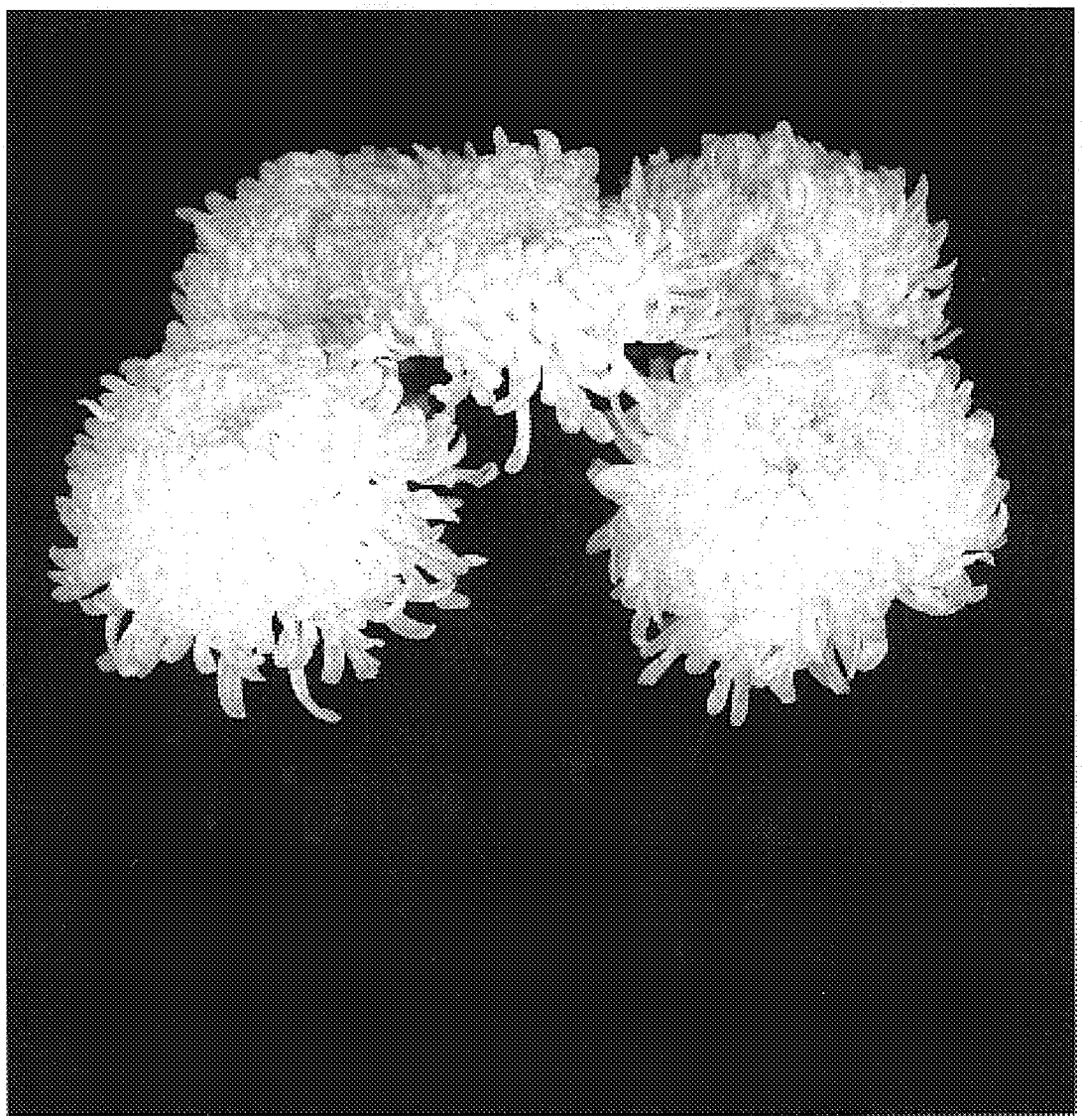

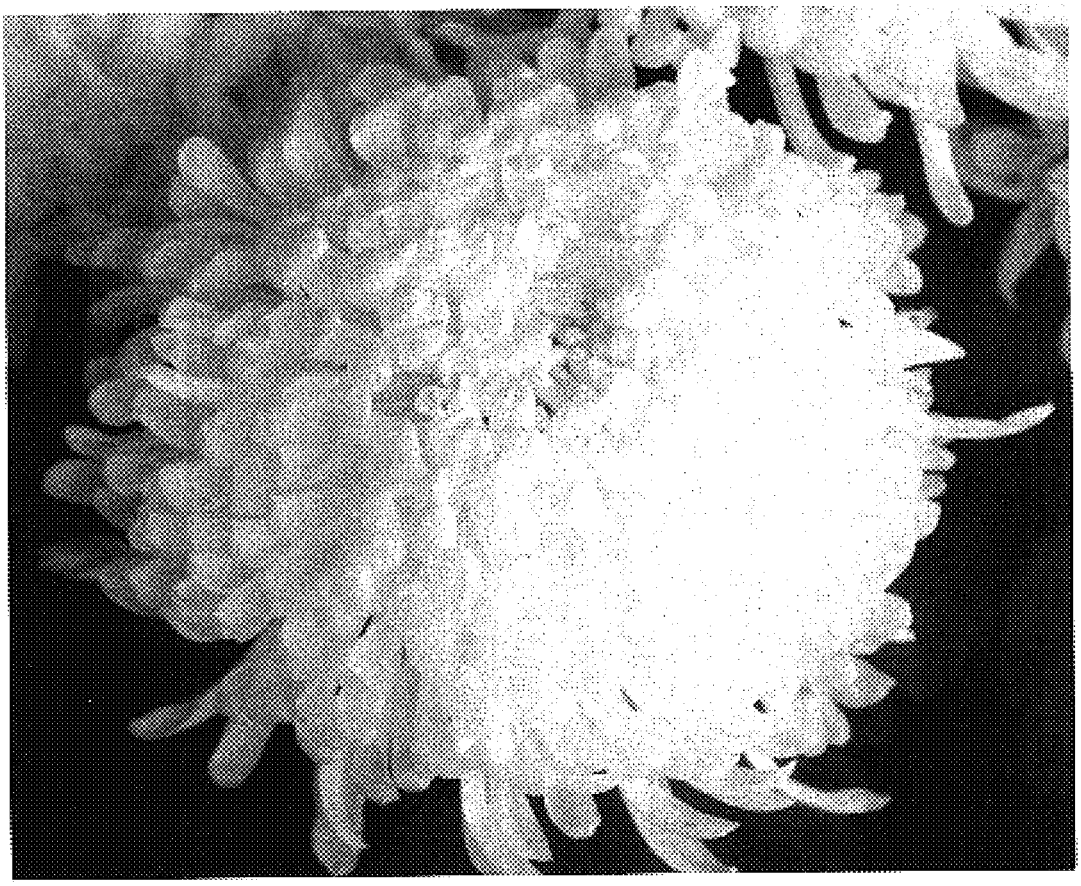

* * * * *